United States Patent [19]

Wenzel et al.

[11] Patent Number: 5,624,960
[45] Date of Patent: *Apr. 29, 1997

[54] ORALLY ADMINISTRABLE DRUGS FOR THE TREATMENT OF CENTRAL DOPAMINE DEFICIENCY CONDITIONS

[75] Inventors: Udo Wenzel, Halle; Günther Weber, Zwickau; Jürgen Metzner, Halle; Alfred Därr, Leipzig; Sabine Freitag, Zwickau, all of Germany; Frank-Ulrich Flöther, Schaffhausen-Herblingen, Switzerland; Frank-Michael Albert, Zwickau, Germany; Margit Haase, Gottingen, Germany; Edith Leistner, Leipzig, Germany

[73] Assignee: ISIS Pharma GmbH, Zwickau, Germany

[*] Notice: The term of this patent shall not extend beyond the expiration date of Pat. No. 5,532,274.

[21] Appl. No.: 472,391

[22] Filed: Jun. 7, 1995

Related U.S. Application Data

[63] Continuation-in-part of Ser. No. 90,163, Feb. 14, 1994, Pat. No. 5,532,274.

[30] Foreign Application Priority Data

Jan. 23, 1991 [DE] Germany ............... 41 01 873.7

[51] Int. Cl.$^6$ ............ A61K 31/195; A61K 31/045; A61K 31/24
[52] U.S. Cl. ............ 514/565; 514/538; 514/567; 514/724; 514/772.2
[58] Field of Search ............... 514/538, 565, 514/567, 724, 772.2

[56] References Cited

U.S. PATENT DOCUMENTS

| | | | |
|---|---|---|---|
| 3,584,113 | 6/1971 | Takebe et al. | 424/19 |
| 3,769,424 | 10/1973 | Bayne | 514/565 |
| 4,424,235 | 1/1984 | Sheth et al. | 514/567 |
| 4,832,957 | 5/1989 | Dempski et al. | 424/469 |
| 4,900,755 | 2/1990 | Dempski et al. | 424/469 |
| 4,983,400 | 1/1991 | Dempski et al. | 424/469 |

FOREIGN PATENT DOCUMENTS

| | | |
|---|---|---|
| 0147780 | 7/1985 | European Pat. Off. . |
| 0253490 | 1/1988 | European Pat. Off. . |
| WO83/00093 | 1/1983 | WIPO . |

OTHER PUBLICATIONS

Noboru et al., "Increasing solubility of tyrosin or 3,4-dihydroxypehnylalanine," *Chemical Abstracts*, 882:10, Abs. No. 64498u Mar. 10, 1975, Columbus, Ohio.

*Primary Examiner*—Kevin E. Weddington
*Attorney, Agent, or Firm*—Marshall, O'Toole, Gerstein, Murray & Borun

[57] ABSTRACT

An orally administrable drug formulation containing levodopa and carbidopa, and having a short release time, is disclosed. The formulation is useful in the treatment of Parkinson's disease.

5 Claims, 3 Drawing Sheets

ORALLY ADMINISTRABLE DRUGS FOR THE TREATMENT OF CENTRAL DOPAMINE DEFICIENCY CONDITIONS

CROSS-REFERENCE TO RELATED APPLICATION

This is a continuation-in-part of U.S. application Ser. No. 08/090,163, filed Feb. 14, 1994, now U.S. Pat. No. 5,532,274.

FIELD OF THE INVENTION

This invention relates to orally administrable drug formulations, which contain a combination of the drugs levodopa and carbidopa in defined proportions, as well as a process for their manufacture. The invention is useful in the pharmaceutical industry and makes available a pharmaceutical preparation which can be used for treatment of Parkinson's disease.

BACKGROUND OF THE INVENTION

Serious disorders of the movement automatism, e.g., Parkinson's disease, occur frequently with increasing age.

The cerebral deficiency of neurotransmitters dopamine in the basal ganglions of the brain of the diseased person, in particular, in the corpus striatum, as a consequence of a nigrostrialis degeneration of unknown etiology necessary for the extra pyramidal motoricity, leads to an imbalance between the dopaminogenic and cholinogenic neurotransmitter systems transmitting dopamine which brings about the coordination of movement.

A substitution of the missing biogenous amine can be achieved by supplying its precursor levodopa, which penetrates the blood-brain barrier; said levodopa being absorbed into the dopaminogenic neurons and decarboxylated into dopamine. (Birkmayer, Hornkiewics, Wien, Klin. Wochenschrift 73 (1961), 787.) It is known that the peripheral dopadecarboxylation of levodopa by the simultaneous oral administration of a suitable decarboxylase inhibitor, e.g., carbidopa (DE-PS 30 12 602, U.S. Pat. No. 3,769,424), or benserazide (DE-PS 32 35 093) is largely suppressed, resulting in a distinct increase of the levodopaserum level, which renders possible a relevant reduction of the therapeutically necessary dosage and a decrease of associated gastrointestinal and cardiovascular side effects.

The manufacture of capsules and film tablets containing levodopa and carbidopa, and tablets capable of floating in the gastric fluid (GB-PS 1 243 474, U.S. Pat. No. 4,424,235, BE-PS 894 376), is known. Furthermore, international standards have required, up to the present, a very fast in vitro liberation (USP XXI). In addition, methods for the manufacture of pharmaceutical preparations, from which the medicinal substances levodopa and carbidopa are released slowly and simultaneously, are known. These pharmaceutical preparations, for example, can be polymer matrices (EP-PS 0 253 490, EP-PS 0 320 051), pellets (DE-PS 38 41 955, EP-PS 0 260 236, EP-PS 0 324 947), or also multi-layered molded shapes (EP-PS 0 302 693, EP-PS 0 314 206).

It is also known that the transformation of a medicinal substance, or of a medicinal substance mixture, into a medicinal formulation is essential for influencing the bioavailability. At the same time, it is known to make manageable very low drug dosages by means of suitable pharmaceutical adjuvants, or, as the case may be, to counteract drug incompatibilities in drug mixtures, or to guarantee the chemical stability of one or several drugs. Furthermore, for the manufacture of tablets, a multitude of procedures are known, the aim of which is to transfer pulverized drugs, or mixtures of pulverized drugs and pharmaceutical adjuvants, into tablets under technical conditions. It is known that, by means of an addition of suitable pharmaceutical adjuvants to the drugs or the drug-adjuvant mixtures, it is possible to influence and change the characteristics of the compositions, e.g., stability, electrostatic charge, flow characteristics and tableting characteristics, as well as their bioavailability.

Also, filling hard gelatin capsules with medicinal substances containing powder mixtures, granules, pellets, and similar materials, has been described.

It is also known that by the addition of polyvinylalcohols, a significant delay of the drug liberation can be obtained (DD-WP A 61 K/309 487.4; U. Meyer, Diss., Berlin 1977), and that, in general, quickly decomposing solid tablets can be manufactured with polyvinyl alcohol (W. Rietschel, "die Tablette," 104, Aulendorf, 1966).

DESCRIPTION

Figure 1:
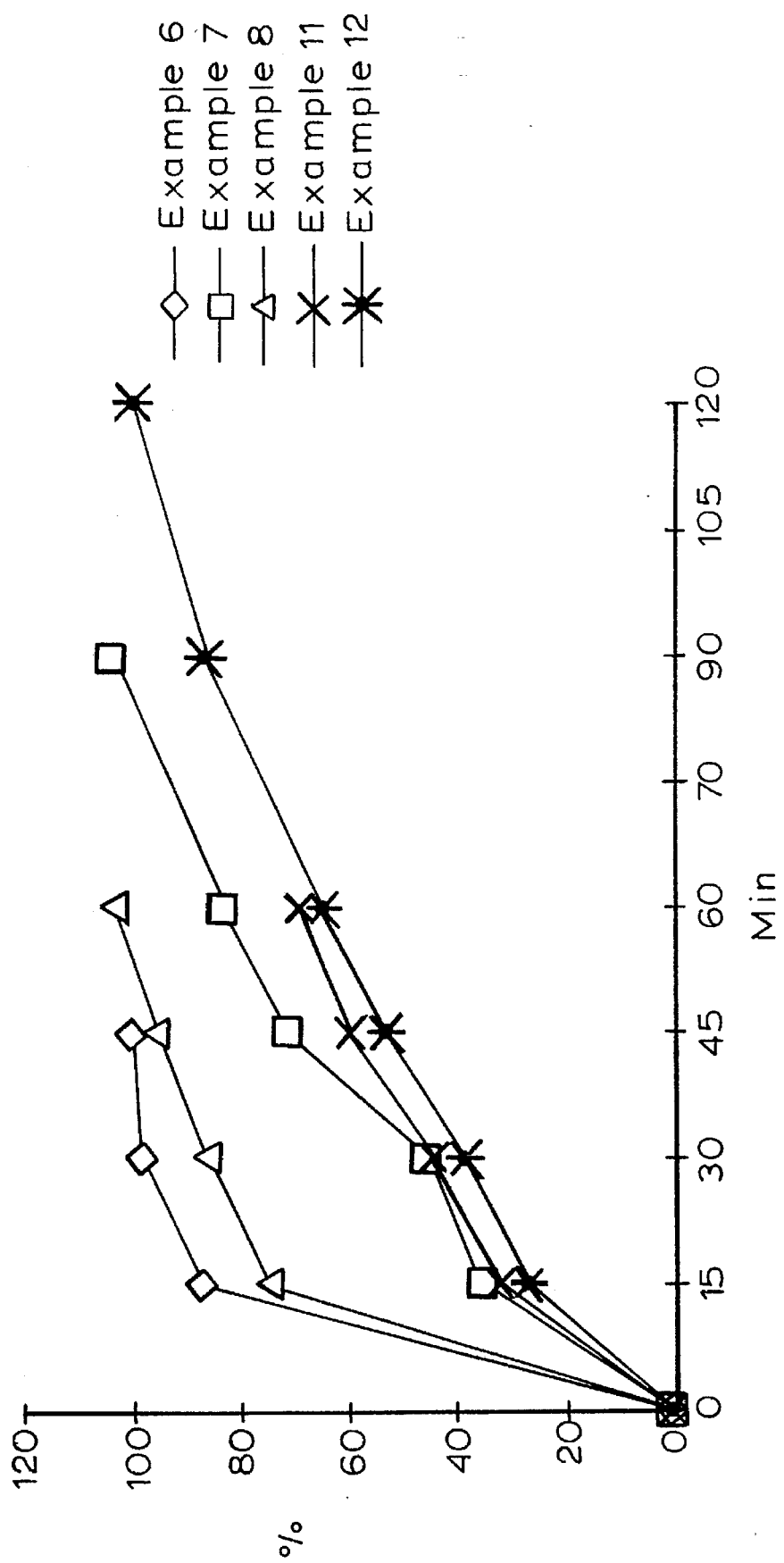
FIG. 1 is a plot of percent (%) in vitro levodopa release versus time (minutes) for the formulations of Examples 6–8, 11, and 12.

The considerable variability, in part, of the clinical picture of Parkinson's disease requires a sensible, individually adjustable medicinal therapy.

On the one hand, drugs must be available to the therapeutic specialist, which correct, by an immediate complete liberation of the drugs levodopa and carbidopa, the transmitter deficiencies which have occurred in the course of a day, and consequently, produce a fast improvement in the patient's total condition.

On the other hand, in a certain number of patients, also as a consequence of the consistent drug release in a long-term therapy with consequent high levodopa plasma levels, undesirable and unpleasant side effects occur which strongly impair the condition.

This invention has the object of developing a medicinal formulation which is periodically administrable by mouth, as well a process for its manufacture, according to which tablets and capsules can be manufactured from levodopa and carbidopa, from which the drugs, in a release period of about 30 to 45 minutes, are controlled and, over a further desired period, are released completely and evenly, but without significant delay.

According to the invention, this object is achieved by mixing 100 to 250 parts by weight of levodopa and 10 to 25 parts by weight of carbidopa with a polymer mixture comprising 0 to 100 parts by weight of a completely saponified polyvinyl alcohol and 100 to 0 parts by weight of a partially saponified polyvinyl alcohol, in proportions of 10% to 200% based on the levodopa and carbidopa. To this drug-polymer mixture, customary pharmaceutical adjuvants are added in an amount which renders it possible to manufacture the respective medicinal formulation in a known manner, e.g., by direct tableting, tableting after granulation with a suitable binding agent, or by filling into hard gelatin capsules.

Preferably, as polyvinyl alcohols, commercial products are used, the k-values of which (Fikentscher, Cellulosechemi 13 (1932), 58), for completely saponified polyvinyl alcohols lie in a range of 40 to 59, and, for partially saponified polyvinyl alcohols, lie in a range of 50 to 59. Particularly suited are completely saponified polyvinyl alcohols with 0 to 3 percent of residual acetyl content, a mean molecular weight of 60,000 to 80,000, a total surface area of 0.1 m$^2$/g to 0.18 m$^2$/g and partially saponified polyvinyl alcohols with 10 to 18 percent of residual acetyl content, a mean molecular weight of 80,000, a total surface area of 0.5 m$^2$/g to 0.69 m$^2$/g and a specific pore volume of 0.2 cm$^3$/g to 0.36 cm$^3$/g.

Surprisingly, it has been found that the mixture according to this invention of the adjuvants and medicinal substances and the simple pharmaceutical-technological processing, which is possible through this, leads to the solution of the problem. It has been found furthermore that the levodopa/carbidopa-medicinal formulations obtained according to this invention by the use of combinations of polyvinyl alcohols of various residual acetyl content release the drugs quickly and completely, but in a variable or controllable manner as required.

The process according to this invention produces a drug formulation which releases both medicinal substances quickly and over a certain period at defined ratios and thus guarantees an optimum bioavailability of the peripheral dopadecarboxylase inhibitor carbidopa and the dopamine precursor levodopa.

Accordingly, it is possible, for certain types of patients to produce, with a minimum expense, medicinal formulations with the optimum release characteristics.

Thus, with the described drug formulation, it is possible to produce levodopa/carbidopa medicinal formulations, having either a swift and complete liberation, or, with an initially delayed liberation, as required.

EXAMPLES

Examples 1-12

Levodopa is mixed with carbidopa, a completely saponified polyvinyl alcohol PVA-1 having a residual acetyl content of 2.5%, a mean molecular weight of 70,000, a total surface area of 0.14 m$^2$/g and a k-value of 55, with a partially saponified polyvinyl alcohol with a residual acetyl content of 15%, with a mean molecular weight of 80,000, with a total surface area of 0.57 m$^2$/g, with a specific pore volume of 0.3 cm$^3$/g and a mean k-value of 55, called PVA 2 in the following, as well as with magnesium stearate, and is directly molded into tablets with a compressing power of 10 to 15 kN.

Tested table formulations: See Table 1

In vitro drug liberation: See Table 2

Example 13

250 g levodopa, 25 g carbidopa, 25 g of a completely saponified polyvinyl alcohol with a residual acetyl content of 3%, a mean molecular weight of 60,000, a total surface area of 0.104 m$^2$/g and a k-value of 45, 100 g cellulose powder with a grain particle size range of <0.16 mm≧65% and <0.05 mm=10% to 30% and 5 g magnesium stearate are mixed and granulated with 100 ml of a 2% gelatin solution in a vortex granulator at 60° C., and are dried to a residual water content of 3% to 4%. The granulate is subsequently brought to a grain size of 1.2 mm by putting it through a sieve, and then molded, with a set mass of 407 mg at a compressing force of 10 to 50 kN.

In vitro drug liberation: See Table 2

Example 14

250 g levodopa, 25 g carbidopa, 94 g cellulose powder with a grain particle size range of <0.26 mm≧65% and <0.05 mm=10% to 30%, 3 g silicon dioxide and 51 g PVA 1 are mixed in a vortex granulator, sprayed with 10 ml of a 20% aqueous citric acid solution, and granulated with 150 ml of a 5% aqueous solution of PVA 1, and simultaneously dried at a temperature of 60° C. to a residual water content of 3% to 4%.

The granulate, by means of sieving, is brought to its maximum grain size of 1.2 mm, mixed with 30 g of tallow and 5 g of magnesium stearate for 15 minutes, and compressed with a compressing force of 10 to 50 kN, into tablets with a set mass of 440 mg.

In vitro drug liberation: See Table 2

Example 15

100 g levodopa, 25 g carbidopa, 16 g PVA 1, 5 g PVA 2, and 3 g of silicon dioxide are mixed in a vortex granulator, sprayed with 10 ml of a 20% citric acid solution, and granulated with 75 ml of 10% of an aqueous solution of PVA 1 and dried simultaneously at a temperature of 60° C. to a residual water content of 3% to 4%.

The granulate, by means of sieving, is brought to its maximum grain size of 1.00 mm, mixed with 90 g of cellulose powder with a grain particle size range of <0.26 mm≧65% and <0.05mm=10% to 30%, 10 g of tallow and 2 g of magnesium stearate for 15 minutes, and filled each with 260 mg into a hard gelatin capsule.

In vitro drug liberation: See Table 2

Example 16

Figure 2:
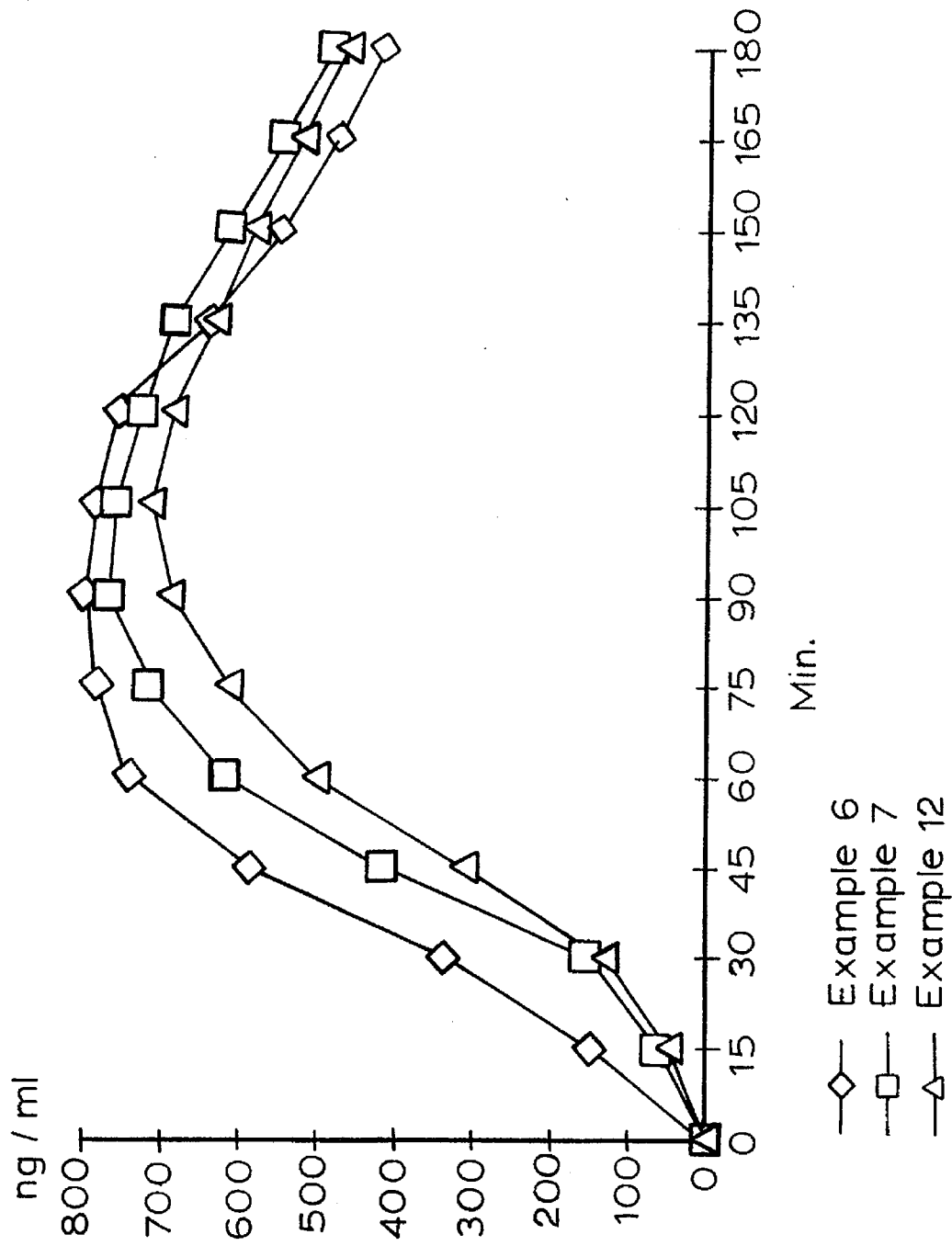
FIGS. 2 and 3 are plots of plasma levodopa level (ng/ml) versus time (minutes) for the formulations of Examples 6, 7, and 12.
Figure 3:
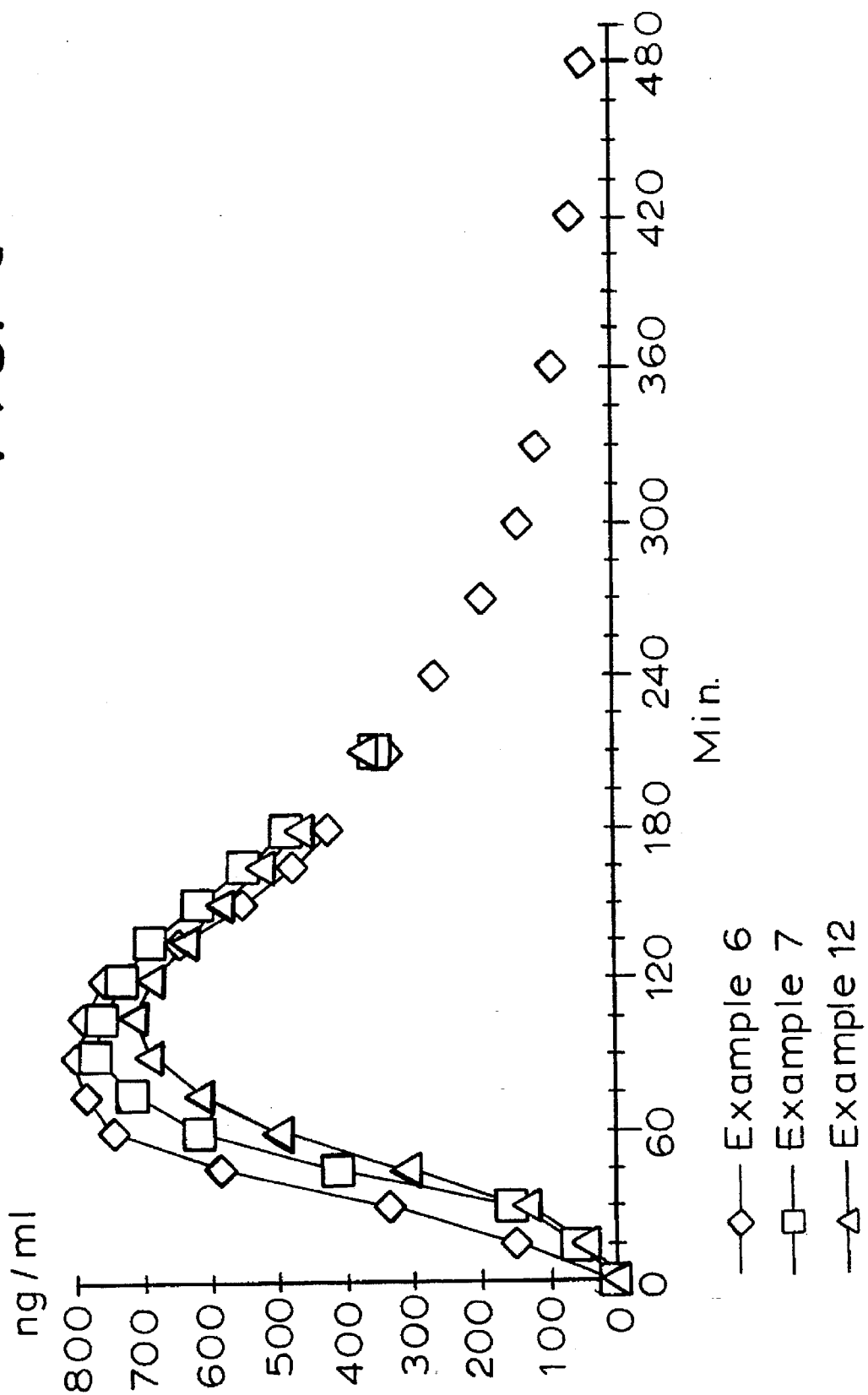

In a random, open cross-over study, twelve healthy test subjects were given one tablet of the compositions of Examples 6, 7, and 12, one time, and the in vitro release of levodopa was determined. The results are illustrated in Tables 1 and 2 and in FIG. 1. The plasma level of levodopa was determined by means of high pressure liquid chromatography (HPLC). The mean value of the plasma level of levodopa were plotted against time. See FIGS. 2 and 3.

TABLE 1

| Example | Levodopa mg | Carbidopa mg | PVA 1 mg | PVA2 mg | Mg-Stearate mg |
|---|---|---|---|---|---|
| 1 | 100 | 10 | 100 | 10 | 5 |
| 2 | 100 | 25 | 100 | 25 | 5 |
| 3 | 150 | 15 | 150 | 15 | 5 |
| 4 | 250 | 25 | 250 | 25 | 5 |
| 5 | 250 | 25 | 25 | 100 | 5 |
| 6 | 250 | 25 | 125 | 0 | 5 |
| 7 | 250 | 25 | 0 | 125 | 5 |
| 8 | 250 | 25 | 100 | 25 | 5 |
| 9 | 100 | 25 | 2.5 | 10 | 5 |
| 10 | 100 | 25 | 12.5 | 50 | 5 |
| 11 | 100 | 25 | 25 | 100 | 5 |
| 12 | 100 | 25 | 50 | 200 | 5 |

TABLE 2

| Example | Drug % | | | | | | | |
|---|---|---|---|---|---|---|---|---|
| Time | Levodopa | | | | Carbidopa | | | |
| min. | 15 | 30 | 45 | 60 | 15 | 30 | 45 | 60 |
| 1 | 82.3 | 95.4 | 99.0 | 101.0 | 81.4 | 93.5 | 99.2 | 100.0 |
| 2 | 85.2 | 93.1 | 100.3 | — | 83.2 | 91.5 | 98.7 | — |
| 3 | 83.6 | 94.4 | 100.1 | — | 84.7 | 86.4 | 99.0 | — |
| 4 | 89.6 | 97.7 | 100.5 | — | 85.3 | 97.6 | 100.4 | — |
| 5 | 42.1 | 69.2 | 86.9 | 100.2 | 33.6 | 70.4 | 91.2 | 98.0 |
| 6 | 87.3 | 98.1 | 100.0 | — | 86.7 | 87.2 | 103.0 | — |
| 7 | 35.2 | 45.4 | 70.9 | 82.9 | 34.9 | 46.6 | 69.2 | 80.1 |
| 8 | 74.7 | 86.3 | 95.1 | 103.0 | 74.2 | 83.3 | 98.4 | — |
| 9 | 47.2 | 75.5 | 93.7 | 98.3 | 42.9 | 75.1 | 92.8 | 98.4 |
| 10 | 43.6 | 73.5 | 100.0 | — | 40.2 | 73.0 | 92.9 | 98.7 |
| 11 | 32.4 | 44.2 | 59.4 | 68.3 | 30.7 | 40.3 | 53.6 | 61.4 |
| 12 | 27.7 | 38.6 | 53.1 | 64.8 | 28.6 | 37.4 | 51.1 | 65.8 |
| 13 | 74.3 | 98.6 | 102.0 | — | 87.0 | 100.0 | — | — |
| 14 | 89.2 | 92.1 | 93.0 | 94.2 | 85.2 | 90.4 | 92.6 | 95.4 |
| 15 | 86.4 | 94.1 | 98.9 | 99.7 | 84.8 | 92.3 | 98.1 | 100.1 |

For examples 7, 11, and 12, the extent of liberation of the drug was tested for periods beyond 60 minutes:

| | Levodopa | | Carbidopa | |
|---|---|---|---|---|
| Example | 90 min. | 120 min. | 90 min. | 120 min. |
| 7 | 103.0 | — | 100.0 | — |
| 11 | 85.6 | 99.1 | 86.3 | 102.2 |
| 12 | 86.4 | 100.0 | 84.5 | 98.6 |

What is claimed is:

1. A drug formulation administrable by mouth for the treatment of central dopamine deficiency conditions, said formulation comprising:

100 to 250 parts by weight levodopa, 10 to 25 parts by weight carbidopa,

10% to 200% based on levodopa and carbidopa, of (a) a polymer mixture consisting of polyvinyl alcohols of various degrees of saponification, or (b) a completely saponified polyvinyl alcohol with a residual acetyl content different from the zero valence, or (c) a partially saponified polyvinyl alcohol, and an appropriate amount of customary galenic adjuvants, said formulation having controlled liberation of levodopa and carbidopa during a short release phase.

2. The drug formulation according to claim 1, wherein the polymer mixture comprises:

a completely saponified polyvinyl alcohol, and a partially saponified polyvinyl alcohol.

3. The drug formulation according to claim 1, characterized in that the completely saponified polyvinyl alcohol with a residual acetyl content different from the zero valence has:

a residual acetyl content of up to 3%, a mean mole mass of 60,000 to 80,000, and a total surface area of 0.1 $m^2/g$ to 0.18 $m^2/g$.

4. The drug formulation according to claim 1, characterized in that the partially saponified polyvinyl alcohol has:

a residual acetyl content of 10% to 18%, a mean mole mass of 80,000, a total surface area of 0.5 $m^2/g$ to 0.69 $m^2/g$, and a specific pore volume of 0.2 $cm^3/g$ to 0.36 $cm^3/g$.

5. The drug formulation according to claim 2 wherein the completely saponified polyvinyl alcohol has:

a residual acetyl content of up to 3%, a mean mole mass of 60,000 to 80,000, as well as a total surface area of 0.1 $m^2/g$ to 0.18 $m^2/g$ and the partially saponified polyvinyl alcohol has:

a residual acetyl content of 10% to 18%, a mean mole mass of 80,000, a total surface area of 0.5 $m^2/g$ to 0.69 $m^2/g$, and a specific pore volume of 0.2 $cm^3/g$ to 0.36 $cm^3/g$.

* * * * *